(12) United States Patent
Lalovic et al.

(10) Patent No.: US 7,087,907 B1
(45) Date of Patent: Aug. 8, 2006

(54) DETECTION OF CONTAMINATION IN IMAGING SYSTEMS BY FLUORESCENCE AND/OR ABSORPTION SPECTROSCOPY

(75) Inventors: Ivan Lalovic, San Francisco, CA (US); Bruno M. LaFontaine, Pleasanton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 277 days.

(21) Appl. No.: 10/770,032

(22) Filed: Feb. 2, 2004

(51) Int. Cl.
  *G01N 21/88* (2006.01)
(52) U.S. Cl. .................................................. 250/461.1
(58) Field of Classification Search .............. 250/461.1
  See application file for complete search history.

(56) References Cited

U.S. PATENT DOCUMENTS

| | | | |
|---|---|---|---|
| 4,393,311 A * | 7/1983 | Feldman et al. ......... 250/459.1 |
| 6,490,031 B1 | 12/2002 | Goldstein et al. ........... 356/121 |
| 6,620,630 B1 | 9/2003 | Kishkovich et al. ........... 438/7 |
| 6,734,443 B1 * | 5/2004 | Zheng et al. ............. 250/492.1 |
| 6,839,375 B1 * | 1/2005 | Lokai et al. .................... 372/92 |
| 6,847,463 B1 * | 1/2005 | Malinowski ................. 356/630 |
| 2005/0133727 A1 * | 6/2005 | Banine et al. ............... 250/397 |
| 2005/0173647 A1 * | 8/2005 | Bakker ....................... 250/372 |

OTHER PUBLICATIONS

"Assessment of Beamline Photo-Induced Contamination for 157 nm Lithography"; International SEMATECH; Technology Transfer #0211433A-ENG, (Nov. 2002).

Meute et al.; "Contamination and Degradation of 157 nm Stepper Optical Components—Field Experience at International SEMATECH"; Proc. SPIE, vol. 4691, p. 724-733 (Jul. 2002).

Keller, AA, ML Kram. Use of Laser Induced Fluorescence to Detect DNAPL and Fluorophore Mixtures In-Situ. Proceedings of the XXVIII IAHR Congress, Graz, Austria (1999).

* cited by examiner

*Primary Examiner*—Constantine Hannaher
(74) *Attorney, Agent, or Firm*—Renner, Otto, Boisselle & Sklar, LLP (57) ABSTRACT

Process and system for detection of contamination in an imaging system, including providing an imaging system having one or more element having a surface for reflecting or refracting first incident radiation; mounting with respect to at least one of the one or more element one or more detector capable of sensing third radiation emitted or transmitted by one or more contaminant on the surface of the one or more element when second radiation is absorbed by the one or more contaminant; applying the first incident radiation and/or the second radiation to the at least one element; and detecting with the one or more detector the third radiation emitted or transmitted by the one or more contaminant.

20 Claims, 3 Drawing Sheets

FIG. 7

DETECTION OF CONTAMINATION IN IMAGING SYSTEMS BY FLUORESCENCE AND/OR ABSORPTION SPECTROSCOPY

TECHNICAL FIELD

The present invention relates generally to the field of integrated circuit manufacture and, more particularly, to a method for detection of contamination on radiation reflective and/or transmissive elements in lithography processes.

BACKGROUND

The formation of various integrated circuit (IC) structures on a wafer often relies on lithography processes, sometimes referred to as photolithography. For instance, patterns can be formed from a photoresist layer by passing light energy through a mask (or reticle) having an arrangement to image the desired pattern onto the photoresist layer. As a result, the pattern is transferred to the photoresist layer. In areas where the photoresist is sufficiently exposed and after a development cycle, portions of the photoresist material can become soluble such that it can be removed to selectively expose an underlying layer (e.g., a semiconductor layer, a metal or metal containing layer, a dielectric layer, etc.). Portions of the photoresist layer not exposed to a threshold amount of light energy will not be removed and serve to protect the underlying layer. The exposed portions of the underlying layer can then be etched (e.g., by using a chemical wet etch or a dry reactive ion etch (RIE)) such that the pattern formed from the photoresist layer is transferred to the underlying layer. Alternatively, the photoresist layer can be used to block dopant implantation into the protected portions of the underlying layer or to retard reaction of the protected portions of the underlying layer. Thereafter, the remaining portions of the photoresist layer can be stripped.

There is a pervasive trend in the art of IC fabrication to increase the density with which various structures are arranged. As a result, there is a corresponding need to increase the resolution capability of lithography systems. As critical dimensions continue to be reduced, the resolution of radiation in lithography systems becomes ever more important. Contaminants on surfaces of radiation reflective and/or transmissive elements in lithography systems can detract from resolution, thus either preventing or reducing the degree of improvements in lithographic systems.

Accordingly, there exists a need in the art for improved methods of detection of contaminants on surfaces of radiation reflective and/or transmissive elements in lithography systems.

SUMMARY OF THE INVENTION

The present invention addresses the problem of detection of contaminants on surface of radiation reflective and/or transmissive elements in lithography systems, by providing method and system for detection of contamination in an imaging system.

According to one embodiment, the invention relates to a process for detection of contamination in an imaging system, including providing an imaging system having one or more element having a surface for reflecting or refracting first incident radiation; mounting with respect to at least one of the one or more element one or more detector capable of sensing third radiation emitted or transmitted by one or more contaminant on the surface of the one or more element when second radiation is absorbed by the one or more contaminant; applying the first incident radiation and/or the second radiation to the at least one element; and detecting with the one or more detector the third radiation emitted or transmitted by the one or more contaminant.

According to another embodiment, the invention relates to an imaging system including a system for detection of contamination in the imaging system, including one or more element having a surface for reflecting or refracting first incident radiation; one or more detector mounted with respect to the one or more element capable of sensing third radiation emitted or transmitted by one or more contaminant on the surface of the one or more element when second radiation is absorbed by the one or more contaminant.

As a result of the process and system of the present invention, a lithography system may be operated while detecting and monitoring contamination of surfaces of radiation reflective and/or transmissive elements in lithography systems, so that when contamination accumulates to too great a degree, the surfaces can be cleaned. As a result, the system can be operated at the highest efficiency for the maximum time.

BRIEF DESCRIPTION OF THE DRAWINGS

These and further features of the present invention will be apparent with reference to the following description and drawings, wherein.

It should be appreciated that for simplicity and clarity of illustration, elements shown in the Figures have not necessarily been drawn to scale. For example, the dimensions of some of the elements are exaggerated relative to each other for clarity. Further, where considered appropriate, reference numerals have been repeated among the Figures to indicate corresponding elements.

DETAILED DESCRIPTION

It should be appreciated that the process steps and structures described below do not form a complete process flow for manufacturing a semiconductor device. The present invention can be practiced in conjunction with semiconductor device fabrication techniques currently used in the art, and only so much of the commonly practiced process steps are included as are necessary for an understanding of the present invention.

The description herein is presented in the exemplary context of fabricating a semiconductor wafer having a semiconductor device formed thereon. Example semiconductor devices include general purpose microprocessors made from thousands or millions of transistors, a flash memory array or any other dedicated circuitry.

However, one skilled in the art will appreciate that the processes and systems described herein can also be applied to the fabrication of any article manufactured using lithography, such as micromachines, disk drive heads, gene chips, micro electro-mechanical systems (MEMS) and so forth.

The processes described herein can provide for the detection of contaminants present on surfaces of transmissive and/or reflective elements of an imaging system, so that contamination can be removed at an optimum time, thus providing a maximum operation of the imaging system prior to shutting down to clean elements thereof, while at the same time avoiding postponement of the cleaning process until a time when the function of the imaging system has been adversely affected by the contamination. As a result, the imaging system can be operated with an increased efficiency.

As used herein, the term "first incident radiation" refers to the primary radiation used in the imaging system, which is to be either transmitted or reflected by the particular element of interest in the imaging system. The elements of interest may be reflective or transmissive, or may be other components of the device which may be subject to contamination and which would suffer deleterious effects therefrom.

As used herein, the term "second radiation" refers to radiation which is at least partially absorbed by and/or which is transmitted and/or which induces fluorescence by contaminants present on a surface of the elements of interest in the imaging system. In one embodiment, the second radiation is the same radiation as the first incident radiation, or is a portion thereof. In another embodiment, the second radiation is radiation different from the first incident radiation, from a different source and having a different wavelength. Such second radiation may have any selected wavelength as needed for detection of a particular contaminant. The second radiation may have a selected wavelength or range of wavelengths, for example, in the IR, visible and/or UV ranges. Thus, the second radiation may have the same wavelength as the first incident radiation but be from a different or separate source, or may represent a portion of the first incident radiation which has been diverted from the source and redirected towards the element of interest so that it does not participate in the primary function of the imaging system but is instead used for the purpose of detecting contamination in accordance with the present invention.

As used herein, "third radiation" is that radiation which is emitted and/or transmitted by a contaminant of interest on the surface of the element of interest in the imaging system. In one embodiment, the third radiation is energy fluoresced by the contaminant, and in another embodiment, the third radiation is energy transmitted by the contaminant. In one embodiment, the third radiation is detected by the detector.

Specific contaminants which may be detected by the process of the present invention depend on the components of the stepper system being operated. Contaminants have been found to arise from gases present in the stepper device (such as process gases or by-products, purge gases, clean room atmosphere, etc.), from resist materials, from materials previously deposited on wafers that are the subject of the operation, from materials of construction of the stepper device itself (such as plasticizers from gaskets, hoses, etc.). The most common sources are the materials of construction and the resist materials.

Examples of specific contaminants include organics, fluorinated alkane- and fluorinated ether-based contaminants, siloxane contaminants, sulfur-based contaminants and iodine-based contaminants. The fluorinated and siloxane contaminants may arise from photoresist materials, sealants, lubricants, adhesives and insulators, which can outgas from such sources under impact of UV radiation, especially 157 nm radiation. The sulfur- and iodine-based contaminants can arise from photoacid generators and from optics materials of construction. Other contaminants may be present from presently unknown sources.

Examples of specific contaminants which may be observed include fluorocarbons such as decafluoropentane ($CF_3CHFCHFCF_2CF_3$), perfluoroheptane ($C_7F_{16}$), ethoxy-nonafluorobutane (($CF_3)_2CFCF_2$—O—$CH_2CH_3$), perfluoro-tributyl amine, isobutyric acid, propylene glycol methyl ether acetate (PGMEA), ethyl pyruvate, ethyl lactate, butyl acetate, heptanone, xylene, alkyl benzenes (e.g., $C_3$–$C_4$), naphthalene, cyclic ($CH_3$–Si—O)$_n$ where n ranges from about 5 to about 9, dodecylmethyl pentasiloxane, tetramethyldisiloxane (TMDS, $C_4H_{14}OSi_2$), hexamethyldisiloxane (HMDS, ($CH_3)_6O_4Si_2$), octamethylcyclotetrasiloxane (OMCTS, ($CH_3)_8O_4Si_4$), various alkyl esters, 2,2,4,-trimethyl-1,3-pentanediol diisobutyrate (TXIB), $C_7$–$C_{15}$ hydrocarbons, dimethyl sulfide, methyl phenyl sulfide, methyl benzene sulfonate, and t-butyl iodobenzene. The silicon-containing contaminants are of particular concern, since formation of $SiO_2$ on lens and other surfaces can be quite detrimental to system performance. Any of the contaminants may reduce transmission of the primary, incident radiation, and so effect operations in a variety of ways. Even contaminants which have minimal direct effect on transmission or other optical properties may detract from performance, by enhancing likelihood of deposition of other, more detrimental contaminants. Thus, it is important to be able to detect the presence of contaminants, so that both preventive and mitigating steps can be taken by the operators. While the foregoing contaminants are specifically identified, these are considered as exemplary only. Many other contaminants may be present and detectable by the methods and devices described herein, and are considered to be within the scope of the invention.

Figure 1:
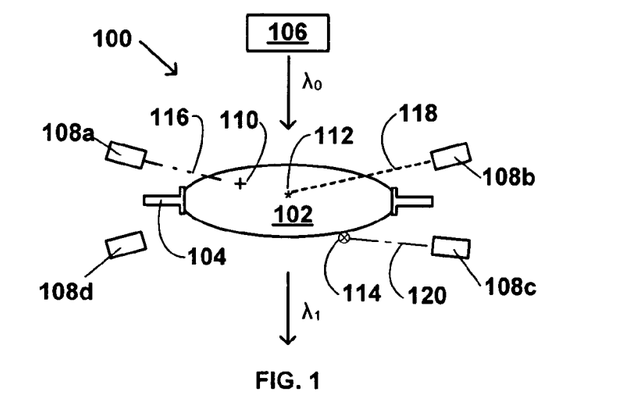
FIG. 1 is a side elevation view of a transmissive element of an imaging system, in accordance with one embodiment of the present invention.

Referring to FIG. 1, there is schematically illustrated a side elevation view of a portion of an imaging system 100, in accordance with one embodiment of the invention. The imaging system 100 includes a transmissive lens 102, a lens mount 104, a source 106 of first incident radiation, $\lambda_0$, and a plurality of detectors 108a, 108b, 108c and 108d. The first incident radiation $\lambda_0$ is provided by the source 106, and in operation of the imaging system 100, the first incident radiation, $\lambda_0$, passes into the lens 102 and emerges as transmitted radiation, $\lambda_1$. The transmitted radiation $\lambda_1$ is referred to by a different reference symbol because it generally will have been altered in some manner by its passage through the lens 102. The detectors 108a–d detect third radiation emitted or not absorbed, i.e., radiation transmitted by the contaminant species of interest, such as one of those described in more detail above. The detectors 108a–d are indicated by different reference numerals to indicate that they may be different detectors, sensitive to different wavelengths of third radiation.

As shown schematically in FIG. 1, contaminants 110 and 112, illustrated as a "+" and a "*", respectively, are present on the upper side of the lens surface. In FIG. 1, a contaminant 114 is also present on the lower side of the lens surface, illustrated as a "⊗". It should be noted that, while the contaminants 110, 112 and 114 are shown as points or spots, it is possible and, in some embodiments, likely, that any such contaminants will be present over larger areas of the surface of the lens 102. Furthermore, the positions of the contaminants are exemplary only. In one embodiment (not shown), a contaminant covers a substantial portion of the surface of the lens 102.

In the embodiment illustrated in FIG. 1, the first incident radiation, $\lambda_0$, strikes the contaminants 110, 112, 114. In this embodiment, the system is passive, in that it does not include a separate source of second radiation for excitation of the contaminants 110, 112, 114, but instead relies upon interaction of the first incident radiation, $\lambda_0$, with the contaminants 110, 112, 114 to generate the third radiation. Thus, in this embodiment, the second radiation is a portion of the first incident radiation. In this embodiment, interaction of the first incident radiation, $\lambda_0$, with the contaminants 110, 112, 114 causes the contaminants to first absorb energy from the first incident radiation, and then to emit energy, as the third radiation, which can be detected by the detectors 108a–d. In one embodiment, the emission of energy by the contaminants 110, 112, 114 when excited by the first incident radiation, is fluorescence, and in another embodiment, the emission of energy by the contaminants 110, 112, 114 is phosphorescence.

The third radiation, emitted from the contaminants 110, 112, 114 is represented in FIG. 1 by lines 116, 118 and 120, respectively. In the embodiment shown in FIG. 1, the third radiation is represented by the line 116 which is emitted by and leads from the contaminant 110 to one of the detectors 108a, while the third radiation is represented by the line 118 which is emitted by and leads from the contaminant 112 to another detector 108b, and the third radiation is represented by the line 120 which is emitted by and leads from the contaminant 114 to a third detector 108c. Although no third radiation is shown going to the detector 108d, this detector may be sensitive to and detect any one of the third radiations, or another third radiation. FIG. 1 illustrates only one embodiment. Any given contaminant may emit energy in any given direction, or in one or more particular direction (depending, for example, on the nature and/or relative orientation of the contaminant to the propagation direction of the first incident radiation). The position of the detectors 108a–d is exemplary in FIG. 1, as is the number of detectors. For the present invention, at least one detector is needed. Additional detectors may be used, for example, to detect multiple wavelengths of fluorescence, or to detect absorption of applied second radiation, in place of or in addition to detection of fluorescence.

As used herein, unless otherwise specifically noted, the term "fluorescence" refers to emission of energy by excited species whether the emission is, strictly speaking, fluorescence or phosphorescence; thus the term "fluorescence" is used generically with respect to excitation-resultant emission phenomena. As is known in the art, fluoresced radiation generally has a longer wavelength, i.e., lower energy, than the excitation wavelength which caused the fluorescence, because some energy is expended in the excitation of electrons in the excited species, and the emitted radiation generally does not have an energy greater than the incident radiation.

The one or more detector, e.g., the detectors 108a–d, may be positioned and oriented as needed to obtain the strongest signal of each third radiation to be separately detected. Thus, some experimentation may be needed to optimize the position(s) and orientation(s) of each of the one or more detector(s). This will depend, for example, on whether the fluorescence or absorption is due to the first incident radiation or to a separately applied second radiation, as will be described below with respect to FIGS. 4–6.

Figure 2:
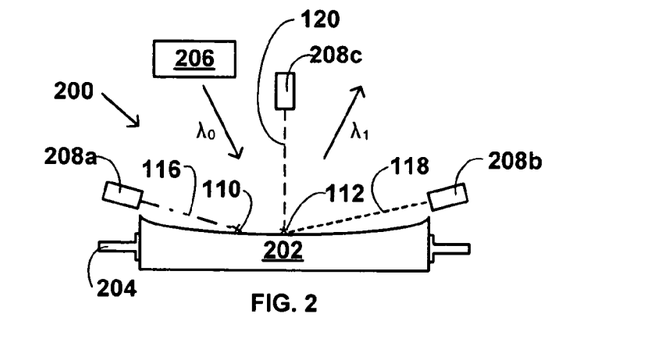
FIG. 2 is a side elevation view of a reflective element of an imaging system, in accordance with another embodiment of the present invention.

The number of detectors 108 may be suitably selected based on the number of species sought to be detected, the number of different wavelengths expected, and whether each detector is capable of detecting radiation of multiple wavelengths. Although four detectors 108a–d are shown in FIG. 1 and three detectors 208a–c are shown in FIG. 2, these are for illustrative purposes, and are not intended to limit the scope of the invention. As noted, one or more detector needs to be present. As will understood, the more detectors, the more information potentially can be obtained, or the information may be obtained in less time.

The detectors should be sensitive to relevant wavelength(s) for the radiation. Thus, for example, if a particular species of concern is known to fluoresce or absorb at a particular wavelength, then at least one detector sensitive to that wavelength should be included for detecting the third radiation of that particular wavelength. Detectors capable of detecting a plurality of discrete wavelengths or ranges of wavelengths are particularly useful; and in one embodiment, a detector capable of scanning through a wider range of wavelengths is particularly useful. In one embodiment, at least one of the one or more detectors is capable of scanning through a range of wavelengths. In one embodiment, at least one of the one or more detector is capable of scanning through the range of infrared and near-infrared wavelengths. In one embodiment, at least one of the one or more detectors is capable of scanning through the range of visible wavelengths. In one embodiment, at least one of the one or more detectors is capable of scanning through the range of ultraviolet wavelengths. In one embodiment, at least one of the one or more detectors is capable of scanning through the range from the infrared through the visible wavelengths. In one embodiment, at least one of the one or more detectors is capable of scanning through the range from the visible through the UV wavelengths. In one embodiment, at least one of the one or more detectors is capable of scanning through the range from the UV through the VUV wavelengths, including the EUV range to less than 10 nm wavelength. In one embodiment, at least one of the one or more detectors is capable of scanning through the range from the EUV through the X-ray wavelengths, including the soft X-ray range to less than 1 nm wavelength, and into the hard X-ray wavelengths of less than 0.1 nm. As will be recognized, one or more specialized detector may be needed to cover various of the foregoing wavelength ranges of the third radiation.

In one embodiment, the number of detectors is at least partially related to the expected or known number of contaminants likely to be found on the surfaces of interest.

The imaging system 100, like the other imaging systems described herein, can be, for example, part of a step-and-repeat exposure system or part of a step-and-scan exposure system, but is not limited to these exemplary systems. The system 100 may include the source 106 which directs light or other first incident radiation $\lambda_0$ to the lens 102 and thence, as transmitted radiation, $\lambda_1$, towards a mask or reticle and/or to a wafer (not shown). The terms "light" and "radiation" are used interchangeably herein, and are intended to refer to electromagnetic radiation having a selected wavelength useful for the particular type of lithography in which the process and system of the present invention are employed. The first incident radiation $\lambda_0$ can have, for example, a deep ultraviolet (DUV) wavelength (e.g., about 248 nm or about 193 nm) or a vacuum ultraviolet (VUV) wavelength (e.g., about 157 nm). In one embodiment, the selected wavelength is in a range from about 11 nm to about 400 nm. In one embodiment, the selected wavelength is about 157 nm. Other embodiments may include radiation of any suitable wavelength, form X-ray through visible to infrared radiation.

In one embodiment, the fluorescence is laser-induced fluorescence. In this embodiment, a second radiation is applied, which here is laser radiation. Suitable systems for laser-induced fluorescence are known in the art. This technique is useful for scanning through a range of wavelengths when a variety of contaminants are thought possibly to be present. This technique is particularly useful in the detection of trace elements which may be present in the contaminants. Laser induced fluorescence depends on the fact that each element emits and absorbs radiation of certain specific wavelengths. The wavelength at which various contaminants are known or can be determined experimentally, and a suitable detector deployed as needed. The detector is capable of detecting radiation emitted by the fluorescing species. The emitted radiation is third radiation in this embodiment.

In one embodiment, the fluorescence is X-ray fluorescence (XRF). In this embodiment, a second radiation is applied, which is X-ray radiation. Suitable systems for X-ray fluorescence are known in the art.

In one embodiment, by analysis of the emitted and/or transmitted second radiation, in comparison to the second radiation arriving at the contaminant of interest (e.g., the first incident radiation arriving at the contaminant 110), a qualitative and/or quantitative analysis of the contaminant can be carried out. In another embodiment, by analysis of the emitted, e.g., fluoresced, third radiation, a qualitative and/or quantitative analysis of the contaminant can be carried out.

Referring next to FIG. 2, there is schematically illustrated a side elevation view of a portion of an imaging system 200, in accordance with a second embodiment of the invention. The imaging system 200 includes a reflective lens 202, a lens mount 204, a source 206 of first incident radiation, $\lambda_0$, and a plurality of detectors 208a, 208b and 208c. The first incident radiation $\lambda_0$ is provided by the source 206, and in operation of the imaging system 200, reflected radiation, $\lambda_0$, exits the reflective lens 202 after being reflected by the lens 202. The reflected radiation $\lambda_0$, is referred to by a different reference symbol because it generally will have been altered in some manner by its reflection by the lens 202. The detectors 208a–c detect third radiation emitted or transmitted, i.e., not absorbed, by the contaminant species of interest, such as one of those described in more detail above. The detectors 208a–c are indicated by different reference numerals to indicate that they may be different detectors, sensitive to different wavelengths of third radiation.

As shown schematically in FIG. 2, contaminants 110 and 112, illustrated as a "+" and a "*", respectively, are present on the reflective side of the lens surface. It should be noted that, while the contaminants 110, 112 are shown as points or spots, it is possible and, in some embodiments, likely, that any such contaminants will be present over larger areas of the surface of the lens 202. As in other embodiment, the positions of the contaminants are exemplary. In one embodiment (not shown), a contaminant covers a substantial portion of the surface of the lens 202.

In the embodiment illustrated in FIG. 2, the first incident radiation, $\lambda_0$, strikes the contaminants 110, 112. In this embodiment, the system is passive, in that it does not include a separate source of second radiation for excitation of the contaminants 110, 112, but instead relies upon interaction of the first incident radiation, $\lambda_0$, with the contaminants 110, 112. Thus, in this embodiment, as in the first embodiment, the second radiation is a portion of the first incident radiation. In this embodiment, interaction of the first incident radiation, $\lambda_0$, with the contaminants 110, 112 causes the contaminants to first absorb energy from the first incident radiation, and then to emit energy, as the third radiation, which can be detected by the detectors 208a, 208b and 208c. In one embodiment, the emission of energy by the contaminants 110, 112 when excited by the first incident radiation, is fluorescence, and in another embodiment, the emission of energy by the contaminants 110, 112 is phosphorescence.

The third radiation, emitted from the contaminants 110, 112 is represented in FIG. 2 by lines 116 and 118, respectively. In the embodiment shown in FIG. 2, the third radiation is represented by the line 116 which is emitted by and leads from the contaminant 110 to one of the detectors 208a, and another third radiation is represented by the line 118 which is emitted by and leads from the contaminant 112 to another detector 208b, and yet another third radiation is represented by the line 120 which is emitted by and leads from the contaminant 112 to a third detector 208c, shown in FIG. 2 as directly above the lens 202. These are exemplary embodiments, and any given contaminant may emit the third radiation in any given direction, or in one or more particular direction (depending, for example, on the nature and/or relative orientation of the contaminant to the propagation direction of the first incident radiation). The positions of the detectors 208a–c are exemplary in FIG. 2, as is the number of detectors.

Figure 3:
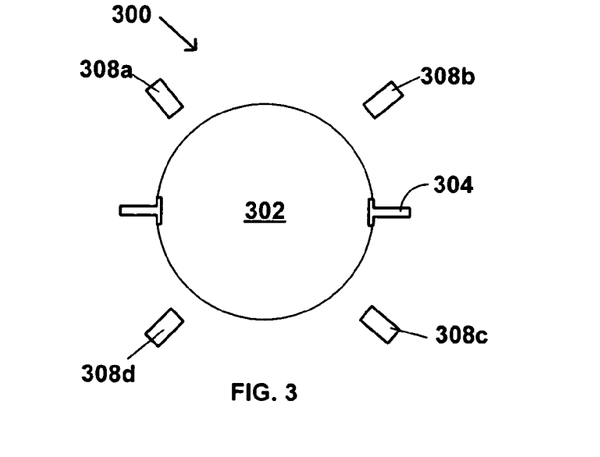
FIG. 3 is a top plan view of a reflective element such as that of FIG. 1, in accordance with an embodiment of the present invention.

Referring next to FIG. 3, there is schematically illustrated a top plan view of a transmitting imaging system 300, similar to the imaging system 100 shown in FIG. 1. The imaging system 300 includes a lens 302, a lens mount 304, and a plurality of detectors 308a–d. The imaging system 300, and the process of this embodiment, operate substantially similar to the foregoing description of the imaging systems 100 and 200. A top plan view is not shown for a reflecting imaging system such as that shown in FIG. 2, but it would appear similar to that shown in FIG. 3, except that the position of the detectors would be different.

In the foregoing embodiments illustrated in FIGS. 1–3, the second radiation is the same as or is a portion of the first incident radiation. That is, the source of the second radiation for excitation of the contaminant is that portion of the first incident radiation which is absorbed by and re-emitted or transmitted by the contaminant. In this embodiment, a high percentage of the first incident radiation is transmitted as it is intended to be through the lens and is available for the intended use of the imaging system. A small fraction, e.g., in one embodiment from about 0.01% to about 10%, and in another embodiment from about 0.1% to about 5%, is absorbed by the contaminant. Here, as elsewhere in the specification and claims, the numerical limits of the disclosed ranges and ratios may be combined. In these passive embodiments, the first incident radiation which is absorbed may be emitted as fluorescence or phosphorescence in any or all directions, or may be transmitted in a direction other than the primary direction of the first incident radiation from its source to the lens.

Figure 4:
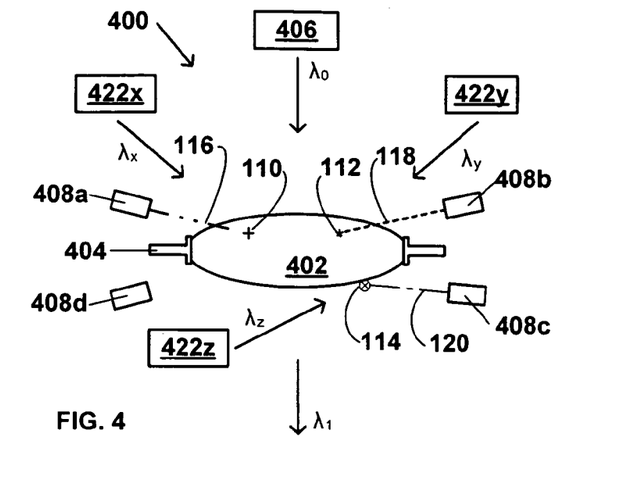
FIG. 4 is a side elevation view of a transmissive element of an imaging system, in accordance with another embodiment of the present invention.

Referring next to FIG. 4, there is schematically illustrated a side elevation view of a portion of an imaging system 400 in accordance with another embodiment of the invention. The imaging system 400 includes a transmissive lens 402, a lens mount 404, a source 406 of first incident radiation, $\lambda_0$, and a plurality of detectors 408a, 408b, 408c and 408d. The first incident radiation $\lambda_0$ is provided by the source 406, and in operation of the imaging system 400, the first incident radiation $\lambda_0$ passes into the lens 402 and emerges as transmitted radiation, $\lambda_1$. The transmitted radiation $\lambda_1$ is referred to by a different reference symbol because it generally will have been altered in some manner by its passage through the lens 402. The detectors 408*a*–*d* detect third radiation emitted or not absorbed, i.e., radiation transmitted, by the species of interest, such as one of those described in more detail above.

As shown schematically in FIG. 4, contaminants 110 and 112, illustrated as a "+" and a "*", respectively, are present on the surface of the lens 402. In FIG. 4, a contaminant 114 is also present on the surface of the lens 402, illustrated as a "⊗". It should be noted that, while the contaminants 110, 112 and 114 are shown as points or spots, it is possible and, in some embodiments, likely, that any such contaminants will be present over larger areas of the surfaces of the lens 402. In one embodiment (not shown), a contaminant covers a substantial portion of the surface of the lens 402. As noted with respect to the other embodiments, the illustrated positions of the contaminants in FIG. 4 is exemplary only.

In the embodiment illustrated in FIG. 4, the lens system further includes three sources of second radiation, shown as sources 422*x*, 422*y* and 422*z*. These sources 422*x*, 422*y* and 422*z* each provide a beam of second radiation, $\lambda_x$, $\lambda_y$, and $\lambda_z$, respectively. The beams of second radiation, $\lambda_x$, $\lambda_y$, and $\lambda_z$, respectively, excite the contaminants 110, 112, 114. In this embodiment, the detection system is active, since it includes separate sources of second radiation for excitation of the contaminants 110, 112, 114. This is in contrast to the embodiment of FIGS. 1–3, in which the detection system passively relies upon interaction of the first incident radiation, $\lambda_0$ with the contaminants 110, 112, 114.

Figure 5:
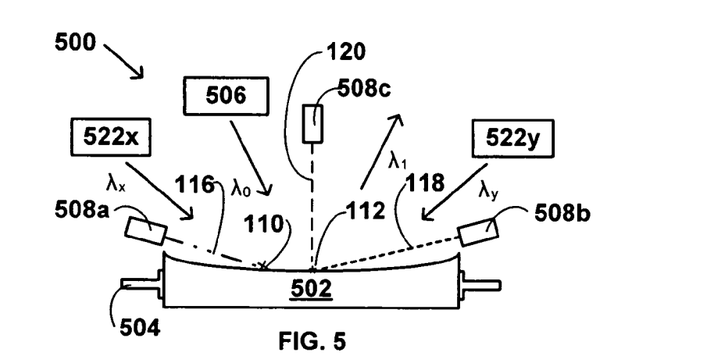
FIG. 5 is a side elevation view of a reflective element of an imaging system, in accordance with yet another embodiment of the present invention.
Figure 6:
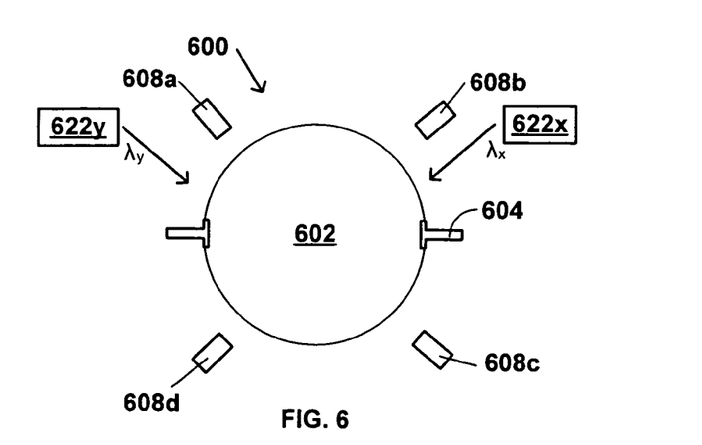
FIG. 6 is a top plan view of a reflective element such as that of FIG. 4, in accordance with an embodiment of the present invention.

Although the embodiment illustrated in FIGS. 4–6 is active, and the embodiment illustrated in FIGS. 1–3 is passive, in one embodiment (see, e.g., FIG. 7 and related text), the passive and active embodiments may be combined or used together in the same imaging system. In such an embodiment, interaction of the first incident radiation, $\lambda_0$, with the contaminants 110, 112, 114 may cause the contaminants to first absorb energy from the first incident radiation, and then to emit energy which can be detected by the detectors 408*a*–*d*, or by other, additional detectors, while at the same time, second radiation is applied for excitation of the same or different contaminants from which third radiation may be suitable detected. In such an embodiment, there is a combined active and passive detection system for detecting contaminants on the surfaces of the lens.

In one embodiment, the emission of energy by the contaminants 110, 112, 114 in FIG. 4 when excited by the second radiation, is fluorescence, and in another embodiment, the emission of energy by the contaminants 110, 112, 114 is phosphorescence.

The third radiation, emitted from the contaminants 110, 112, 114 is represented in FIG. 4 by lines 116, 118 and 120, respectively. In the embodiment shown in FIG. 4, the third radiation is represented by the line 116 which is emitted or transmitted by and leads from the contaminant 110 to one of the detectors 408*a*, and another third radiation is represented by the line 118 which is emitted or transmitted by and leads from the contaminant 112 to another detector 408*b*, and yet another third radiation is represented by the line 120 which is emitted or transmitted by and leads from the contaminant 114 to a third detector 408*c*. FIG. 4 illustrates only one embodiment. Any given contaminant may emit energy in any given direction, or in one or more particular direction (depending, for example, on the nature and/or relative orientation of the contaminant to the propagation direction of the first incident radiation) or in all directions. The position of the detectors 408*a*–*d* is merely exemplary in FIG. 4, as is the number of detectors. Although no third radiation is shown going to the detector 408*d*, this detector may be sensitive to and detect any one of the third radiations, or another third radiation.

In one embodiment, by analysis of the transmitted second radiation, in comparison to the second radiation arriving at the contaminant of interest (e.g., the second radiation from the source 422*x* arriving at the contaminant 110), a qualitative and/or quantitative analysis of the contaminant can be carried out. In another embodiment, by analysis of the emitted, e.g., fluoresced, third radiation, a qualitative and/or quantitative analysis of the contaminant can be carried out.

Referring next to FIG. 5, there is schematically illustrated a side elevation view of a portion of an imaging system 500, in accordance with another embodiment of the invention. The imaging system 500 includes a reflective lens 502, a lens mount 504, a source 506 of first incident radiation, $\lambda_0$, and a plurality of detectors 508*a*, 508*b* and 508*c*. The first incident radiation $\lambda_0$ is provided by the source 506, and in operation of the imaging system 500, reflected radiation, $\lambda_1$, exits the reflective lens 502 after being reflected by the lens 502. The reflected radiation $\lambda_1$, is referred to by a different reference symbol because it generally will have been altered in some manner by its reflection by the lens 502. The detectors 508*a*–*c* detect third radiation emitted or transmitted, i.e., not absorbed, by the contaminant species of interest, such as those described in more detail above. The detectors 508*a*–*c* are indicated by different reference numerals to indicate that they may be different detectors, sensitive to different wavelengths of third radiation.

As shown schematically in FIG. 5, contaminants 110 and 112, illustrated as a "+"and a "*", respectively, are present on the reflective side of the lens surface. It should be noted that, while the contaminants 110, 112 are shown as points or spots, it is possible and, in some embodiments, likely, that any such contaminants will be present over larger areas of the surface of the lens 502. The position of the contaminants is exemplary only. In one embodiment (not shown), a contaminant covers a substantial portion of the surface of the lens 502.

In the embodiment illustrated in FIG. 5, the lens system further includes two sources of second radiation, shown as sources 522*x* and 522*y*. These sources 522*x*, 522*y* each provide a beam of second radiation, $\lambda_x$ and $\lambda_y$, respectively. The beams of second radiation, $\lambda_x$ and $\lambda_y$, respectively, excite the contaminants 110 and 112. In this embodiment, the detection system is active, since it includes separate sources of second radiation for excitation of the contaminants 110, 112. This is in contrast to the embodiment of FIGS. 1–3, in which the detection system passively relies upon interaction of the first incident radiation, $\lambda_0$, with the contaminants 110, 112 (and 114 in FIG. 1).

The third radiation, emitted from the contaminants 110, 112 is represented in FIG. 5 by lines 116 and 118, respectively. In the embodiment shown in FIG. 5, the third radiation is represented by the line 116 which is emitted or transmitted by and leads from the contaminant 110 to one of the detectors 508*a*, and another third radiation is represented by the line 118 which is emitted or transmitted by and leads from the contaminant 112 to another detector 508*b*, and yet another third radiation is represented by the line 120 which is emitted or transmitted by and leads from the contaminant 112 to another detector 508*c*, shown in FIG. 5 as directly above the lens 502. These are exemplary embodiments, and any given contaminant may emit the third radiation in any given direction, or in one or more particular direction (depending, for example, on the nature and/or relative orientation of the contaminant to the propagation direction of the first incident radiation). The positions of the detectors 508a–c are exemplary in FIG. 5, as is the number of detectors.

Referring next to FIG. 6, there is schematically illustrated a top plan view of a transmitting imaging system 600, similar to the imaging system 400 shown in FIG. 4. The imaging system 600 includes a lens 602, a lens mount 604, and a plurality of detectors 608a–d. In addition to the foregoing components, the imaging system illustrated in FIG. 6 also includes separate sources of second radiation, sources 622 and 622y. These sources of second radiation operate substantially similarly to the sources of second radiation 422x, 422y and 422z, described above with respect to FIG. 4, and is similar to those described with respect to FIG. 5. The imaging system 600, and the process of the present invention, operate substantially similar to the foregoing description of the imaging systems 400 and 500. A top plan view is not shown for a reflecting imaging system such as that shown in FIG. 5, but it would appear similar to that shown in FIG. 6, except that the position of the detectors would be different.

In the foregoing embodiments illustrated in FIGS. 4–6, the second radiation is provided from one or more source separate from the first incident radiation. Thus, this embodiment is an active detection system, in that it actively provides one or more separate source of the second radiation for detection of the contamination. That is, these sources of the second radiation for excitation of the contaminants are other than a portion of the first incident radiation, as in the case of the embodiments shown in FIGS. 1–3, which are passive detection systems. As noted above, in one embodiment, the lens system may include both passive and active detection systems in accordance with the present invention, one example of which is described in the following.

Figure 7:
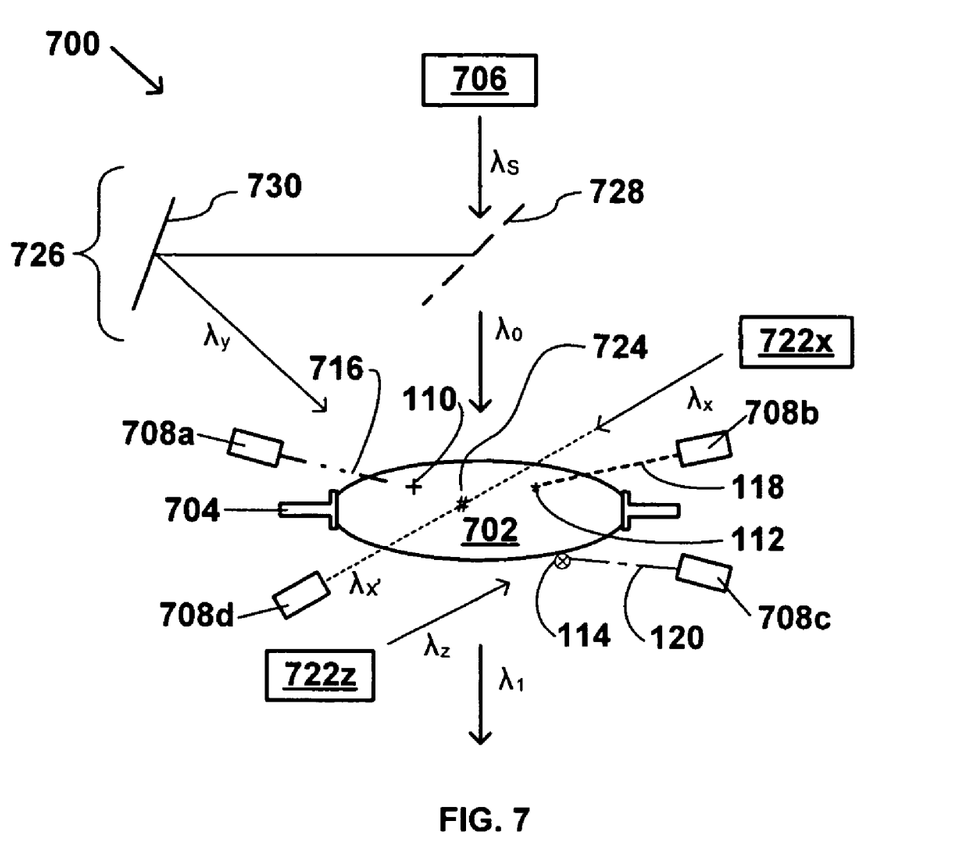
FIG. 7 is a side elevation view of a transmissive element of an imaging system, in accordance with another embodiment of the present invention.

Referring next to FIG. 7, there is schematically illustrated a side elevation view of a portion of an imaging system 700, in accordance with another embodiment of the invention. The imaging system 700 includes a transmissive lens 702, a lens mount 704, a source 706 of first incident radiation, $\lambda_0$, and a plurality of detectors 708a, 708b, 708c and 708d. The first incident radiation $\lambda_0$ is provided by the source 706, and in operation of the imaging system 700, the first incident radiation, $\lambda_0$, passes into the lens 702 and emerges as transmitted radiation, $\lambda_1$. As in other embodiments, the transmitted radiation $\lambda_1$ is referred to by a different reference symbol because it generally will have been altered in some manner by its passage through the lens 702. The detectors 708a–d detect third radiation emitted or transmitted, i.e., not absorbed, by the one or more contaminant species of interest, such as one of those described in more detail above. The detectors 708a–d are indicated by different reference numerals to indicate that they may be different detectors, sensitive to different wavelengths of third radiation.

As shown schematically in FIG. 7, contaminants 110, 112 and 114, illustrated as "+", "*" and "⊗", respectively, are present on the lens surface. In addition, another contaminant 724, indicated by "#" is shown on the surface of the lens 702. It should be noted that, while the contaminants 110, 112, 114 and 724 are shown as points or spots, it is possible and, in some embodiments, likely, that any such contaminants will be present over larger areas of the surface of the lens 702. In one embodiment (not shown), a contaminant covers a substantial portion of the surface of the lens 702. As in all embodiments, the illustrated positions of the contaminants are exemplary only.

In the embodiment illustrated in FIG. 7, the lens system further includes three sources of second radiation, shown as sources 722x, 722z and 726. Each of these sources 722x, 722z and 726 provides a beam of second radiation, $\lambda_x$, $\lambda_z$ and $\lambda_y$, respectively. The beams of second radiation, $\lambda_x$, $\lambda_z$ and $\lambda_y$, respectively, excite the contaminants 724, 114 and 110, as described in the following.

In one embodiment shown in FIG. 7, a first source of second radiation is the source 722x. As shown in FIG. 7, in this embodiment, the second radiation, $\lambda_x$, emitted by the source 722x, strikes the contaminant 724 indicated as "#". Some of the second radiation $\lambda_x$ is absorbed by the contaminant 724, and the remainder of the second radiation $\lambda_x$ is emitted from or transmitted by the contaminant 724 as third radiation $\lambda_{x'}$. The third radiation x, emitted from or transmitted by the contaminant 724 is then detected by the detector 708d, as shown in FIG. 7. This is an example of a contaminant which is detected by application of a second radiation, such as IR, visible or UV radiation, in which a portion of the second radiation is absorbed and a portion of the second radiation is transmitted by the contaminant. By analysis of the transmitted second radiation, in comparison to the second radiation emitted by the source 722x, a qualitative and/or quantitative analysis of the contaminant 724 can be carried out.

In another embodiment shown in FIG. 7, a second source 726 of second radiation, indicated by the bracket, is provided. In this embodiment, the second source 726 includes a half-mirror 728 and a mirror 730. In operation of this embodiment, a portion of the first incident radiation, $\lambda_s$, is diverted by the half-mirror 728 to the mirror 730, and is in turn reflected towards the lens 702 as second radiation $\lambda_y$. In the embodiment shown in FIG. 7, the second radiation $\lambda_y$ is directed toward the contaminant 110. In one embodiment, the second radiation $\lambda_y$ excites the contaminant 110, causing it to emit third radiation 716 which is detected by the detector 708a. In one embodiment, the third radiation 716 is fluoresced radiation. In another embodiment, the third radiation 716 is transmitted radiation. It should be understood that in an embodiment in which the third radiation is transmitted, the detector 708a or another detector may need to be repositioned with respect to the contaminant 110, the lens 702 and the mirror 726 from the positions shown in FIG. 7.

In one embodiment, by analysis of the transmitted second radiation, in comparison to the second radiation arriving at the contaminant of interest (e.g., the second radiation reflected by the mirror 726 arriving at the contaminant 110), a qualitative and/or quantitative analysis of the contaminant can be carried out. In another embodiment, by analysis of the emitted, e.g., fluoresced, third radiation, a qualitative and/or quantitative analysis of the contaminant can be carried out.

The contaminant 112 is excited by the primary incident radiation, $\lambda_0$, as in the embodiments shown and described with respect to FIG. 1. The description of the excitation of the contaminant 112 by the primary incident radiation, $\lambda_0$, and the detection of the emitted or transmitted radiation 118 is the same in this embodiment as in the embodiment of FIG. 1, and will not be further described here.

The contaminant 114 is excited by second radiation, $\lambda_z$, provided by the source 722z as in the embodiment described above with respect to FIG. 4. The description of the excitation of the contaminant 114 by the second radiation, $\lambda_z$, and the detection of the emitted or transmitted radiation 120 is the same in this embodiment as in the embodiment of FIG. 4, and will not be further described here.

Thus, in this FIG. 7 embodiment, the detection system is both active and passive, since it includes separate sources of second radiation for excitation of the contaminants 724, 110 and 114, while the contaminant 112 is excited by the primary incident radiation and is thus passively detected.

The foregoing are exemplary embodiments, and any given contaminant may emit the third radiation in any given direction, or in one or more particular direction (depending, for example, on the nature and/or relative orientation of the contaminant to the propagation direction of the excitatory radiation, i.e., the first incident radiation or the particular second radiation) or in all directions. As in the other embodiments described herein, the positions of the detectors 708a–d are merely exemplary in FIG. 7, as is the number of detectors.

Although particular embodiments of the invention have been described in detail, it is understood that the invention is not limited correspondingly in scope, but includes all changes, modifications and equivalents coming within the spirit and terms of the claims appended hereto.

INDUSTRIAL APPLICABILITY

The present invention relates generally to the field of integrated circuit manufacture and, more particularly, to a process and system for detection of contamination of surfaces of radiation transmissive or reflective elements in imaging systems used in lithography processes. The present invention provides a solution to problems including detection of contaminants, and determination of the optimal time to shut down fabrication processing for cleaning, while avoiding loss of resolution and poor quality products resulting from postponing such cleaning for too long a time. The present invention thus advances the art towards future generations of increased density with which various structures are arranged on semiconductor wafers. The present invention responds to the need to increase the resolution capability of lithography systems, to enable such increased densities.

What is claimed is:

1. A process for detection of contamination in an imaging system, comprising
    providing an imaging system having one or more element having a surface for reflecting or refracting first incident radiation;
    mounting with respect to at least one of the one or more element one or more detector capable of sensing third radiation emitted or transmitted by one or more contaminant on the surface of the one or more element when second radiation is absorbed by the one or more contaminant;
    applying the first incident radiation and/or the second radiation to the at least one element; and
    detecting with the one or more detector the third radiation emitted or transmitted by the one or more contaminant wherein the contaminant comprises one or more of an organic contaminant, a fluorinated alkane-based contaminant, a fluorinated ether-based contaminant, a siloxane contaminant, a sulfur-based contaminant and an iodine-based contaminant.

2. A process as in claim 1 wherein the second radiation is the same radiation as the first incident radiation.

3. A process as in claim 1 wherein the second radiation is separately applied from the first incident radiation.

4. A process as in claim 1 wherein the third radiation is fluorescent radiation generated by the contaminant when the one or more contaminant absorbs the first incident radiation and/or the second radiation.

5. A process as in claim 1 wherein the third radiation is the first incident radiation and/or the second radiation transmitted by the one or more contaminant after a portion has been absorbed by the one or more contaminant.

6. A process as in claim 1 wherein the detector is sensitive to one or more of the first incident radiation, the second radiation and the third radiation.

7. A process as in claim 1 wherein each of the one or more detectors is mounted with respect to the imaging system so that the detectors do not substantially interfere with propagation of the first incident radiation through the imaging system.

8. A process as in claim 1 wherein the detecting is carried out during real-time use of the imaging system in a fabrication process.

9. A process as in claim 1 wherein the first incident radiation is 193 nm radiation, 157 nm radiation, 13.4 nm radiation or X-radiation.

10. A process as in claim 1 wherein the second incident radiation is one or more of infrared, visible, UV, VUV or X-radiation.

11. An imaging system including a device for detection of contamination in the imaging system, comprising
    one or more element having a surface for reflecting or refracting first incident radiation;
    one or more detector mounted with respect to the one or more element capable of sensing third radiation emitted or transmitted by one or more contaminant on the surface of the one or more element when second radiation is absorbed by the one or more contaminant
    wherein the contaminant comprises one or more of an organic contaminant, a fluorinated alkane-based contaminant, a fluorinated ether-based contaminant, a siloxane contaminant, a sulfur-based contaminant and an iodine-based contaminant.

12. An imaging system as in claim 11 wherein the second radiation is the same radiation as the first incident radiation.

13. An imaging system as in claim 11 wherein the second radiation is separately applied from the first incident radiation.

14. An imaging system as in claim 11 wherein the third radiation is fluorescent radiation generated by the contaminant when the one or more contaminant absorbs the first incident radiation and/or the second radiation.

15. An imaging system as in claim 11 wherein the third radiation is the first incident radiation and/or the second radiation transmitted by the one or more contaminant after a portion has been absorbed by the contaminant.

16. An imaging system as in claim 11 wherein the detector is sensitive to one or more of the first incident radiation, the second radiation and the third radiation.

17. An imaging system as in claim 11 wherein each of the one or more detectors is mounted with respect to the imaging system so that the detectors do not substantially interfere with propagation of the first incident radiation through the imaging system.

18. An imaging system as in claim 11 wherein the detector is used to detect contaminants during real-time use of the imaging system in a fabrication process.

19. An imaging system as in claim 11 wherein the first incident radiation is 193 nm radiation, 157 nm radiation, 13.4 nm radiation or X-radiation.

20. An imaging system as in claim 11 wherein the second incident radiation is one or more of infrared, visible, UV, VUV or X-radiation.

* * * * *

UNITED STATES PATENT AND TRADEMARK OFFICE
CERTIFICATE OF CORRECTION

PATENT NO. : 7,087,907 B1
APPLICATION NO. : 10/770032
DATED : August 8, 2006
INVENTOR(S) : Lalovic et al.

It is certified that error appears in the above-identified patent and that said Letters Patent is hereby corrected as shown below:

Col. 7, ln. 41, replace "reflected radiation $\lambda_{O'}$" with --reflected radiation $\lambda_{1'}$--.

Col. 7, ln. 43, replace "reflected radiation $\lambda_{O'}$" with --reflected radiation $\lambda_{1'}$--.

Col. 11, ln. 13, replace "sources 622 and" with --sources 622x and--.

Col. 12, ln. 13, replace "radiation x, emitted" with --radiation $\lambda_{x'}$ emitted--.

Signed and Sealed this

Thirty-first Day of October, 2006

JON W. DUDAS
*Director of the United States Patent and Trademark Office*